(12) United States Patent
Mandal et al.

(10) Patent No.: US 11,147,817 B2
(45) Date of Patent: Oct. 19, 2021

(54) PHARMACEUTICAL COMPOSITION OF PEMETREXED

(71) Applicant: FTF Pharma Private Limited, Ahmedabad (IN)

(72) Inventors: Jayanta Kumar Mandal, Ahmedabad (IN); Sandip Pareshbhai Mehta, Ahmedabad (IN)

(73) Assignee: FTF PHARMA PRIVATE LIMITED, Ahmedabad (IN)

( * ) Notice: Subject to any disclaimer, the term of this patent is extended or adjusted under 35 U.S.C. 154(b) by 0 days.

(21) Appl. No.: 17/127,278

(22) Filed: Dec. 18, 2020

(65) Prior Publication Data

US 2021/0100804 A1    Apr. 8, 2021

Related U.S. Application Data

(63) Continuation of application No. 15/533,374, filed as application No. PCT/IB2015/052223 on Mar. 26, 2015.

(51) Int. Cl.
| | | |
|---|---|---|
| A61K 31/519 | (2006.01) |
| A61K 9/00 | (2006.01) |
| A61K 47/18 | (2017.01) |
| A61K 47/20 | (2006.01) |
| A61K 9/08 | (2006.01) |
| A61P 35/00 | (2006.01) |

(52) U.S. Cl.
CPC .......... *A61K 31/519* (2013.01); *A61K 9/0019* (2013.01); *A61K 9/08* (2013.01); *A61K 47/18* (2013.01); *A61K 47/183* (2013.01); *A61K 47/20* (2013.01); *A61P 35/00* (2018.01)

(58) Field of Classification Search
CPC .................................................... A61K 31/519
See application file for complete search history.

(56) References Cited

U.S. PATENT DOCUMENTS

| | | | |
|---|---|---|---|
| 5,344,932 A | 9/1994 | Taylor | |
| 6,686,365 B2 * | 2/2004 | Riebesehl | A61K 45/06 514/262.1 |

FOREIGN PATENT DOCUMENTS

| | | |
|---|---|---|
| IN | 336585 | 5/2020 |
| WO | WO-2012015810 A2 | 2/2012 |
| WO | WO-2013144814 A1 | 10/2013 |

OTHER PUBLICATIONS

International Search Report and Written Opinion for International Application No. PCT/IB2015/052223, European Patent Office, Netherlands, dated Jul. 14, 2015, 8 pages.

* cited by examiner

*Primary Examiner* — Rei Tsang Shiao
(74) *Attorney, Agent, or Firm* — Sterne, Kessler, Goldstein & Fox P.L.L.C.

(57) ABSTRACT

The present invention relates to pharmaceutical composition comprising pemetrexed, a ready to use injection comprising pemetrexed. Liquid composition of pemetrexed comprises head space oxygen less than 5%, dissolved oxygen less than 2 ppm and individual impurity level less than 0.2%.

18 Claims, No Drawings

PHARMACEUTICAL COMPOSITION OF PEMETREXED

FIELD OF INVENTION

The present invention relates to a pharmaceutical composition comprising pemetrexed, in the form of ready to use injection. Liquid composition of pemetrexed comprises head space oxygen less than 5%, dissolved oxygen less than 2 ppm and individual impurity level less than 0.5%.

BACKGROUND OF INVENTION

The present invention relates to pharmaceutical composition of pemetrexed, in particular, a ready to use injection comprising pemetrexed. Further, invention relates to a liquid composition comprising pemetrexed, antioxidant and pharmaceutically acceptable excipients.

Pemetrexed disodium is chemically described as L-Glutamic acid, N-[4-[2-(2-amino-4,7-dihydro-4-oxo-1H-pyrrolo[2,3-d]pyrimidin-5-yl)ethyl]benzoyl]-disodium salt heptahydrate, represented by the chemical structure of Formula (I).

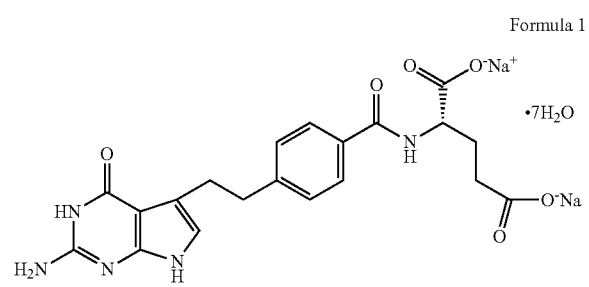

Formula 1

Pemetrexed is an anti-folate anti-neoplastic agent that exerts its action by disrupting folate-dependent metabolic processes essential for cell replication. It is believed to work by inhibiting three enzymes that are required in purine and pyrimidine biosynthesis-thymidylate synthase (TS), dihydrofolate reductase (DHFR), and glycinamide ribonucleotide formyl transferase (GARFT). Pemetrexed is available in the market under the brand name ALIMTA®.

U.S. Pat. No. 5,344,932 describes pemetrexed, its related compounds and pharmaceutically acceptable cation and provide that the compounds claimed therein can be administered parenterally.

It is disclosed in U.S. Pat. No. 6,686,365 that a simple, isotonic saline solution of pemetrexed is not pharmaceutically acceptable for commercial purpose due to degradation of the solution to form unacceptable related substances and they prepared ready to use liquid composition of pemetrexed using antioxidant monothioglycerol, L-cysteine, and thioglycolic acid. In the present invention it is now prepared ready to use, liquid solutions of pemetrexed prepared using antioxidants along with controlled oxygen exposer. Surprisingly the composition disclosed in US '365 was found to be stable only at controlled temperature or refrigeration. However, composition of the present invention improved to prepare the robust formulation by terminal sterilization process. Now achieved formulation is stable at room temperature with adequate shelf life.

DETAILED DESCRIPTION OF INVENTION

Present invention relates to a ready to use, stable liquid composition of pemetrexed can be stored at room temperature and more acceptable in the treatment. Further novelty in the present invention is solutions of pemetrexed prepared using antioxidants along with controlled oxygen exposer. This controlled oxygen is head space oxygen (HSO) less than 5% and dissolved oxygen (OD) less than 2 ppm. Further, liquid composition of the present invention comprises individual impurity level in the final product less than 0.2%. The product is manufactured through a simplified process of solubilisation and a standard/conventional terminal sterilization by autoclaving/steam sterilization with $F_0$ value 1-30 min.

Even after autoclaving the characteristic of the formulation remain stable throughout the shelf life the product at normal room temperature condition.

To prove the novelty of the present invention we carried out practical of four types.
1. With DO less than 2 ppm+With HSO less than 5%
2. With DO less than 2 ppm+With HSO more than 5%
3. With DO more than 2 ppm+With HSO less than 5%
4. With DO more than 2 ppm+With HSO more than 5%

Here all four formulations are terminally sterilized by steam sterilization with $F_0$ value 1-30 min. and the best result we achieved when there is combination of DO less than 2 ppm, HSO less than 5% and terminal sterilization by steam sterilization with $F_0$ value 1-30 min. The result below focus more on the achievement of the present invention that is individual maximum impurity is less than 0.5% and total impurity less than 1%.

Results of Trials:

| Test | Spec | Initial | DO < 2 ppm + HSO < 5% 50° C./75%/1M | DO < 2 ppm + HSO > 5% 50° C./75%/1M |
|---|---|---|---|---|
| Maximum Individual Impurity | | | 0.18 | 0.25 |
| Total Impurity | NMT 1% | 0.42 | 0.92 | 1.4 |

| Test | Spec | Initial | DO > 2 ppm + HSO < 5% 50° C./75%/1M | DO > 2 ppm + HSO > 5% 50° C./75%/1M |
|---|---|---|---|---|
| Maximum Individual Impurity | | | 0.21 | 0.30 |
| Total Impurity | NMT 1% | 0.60 | 1.10 | 3.30 |

With combination of DO less than 2 ppm, HSO less than 5% and terminal sterilization one batch continued for stability of 3M and 6M and achieved results are as below:

| DO < 2 ppm + HSO < 5% | 40° C./75%/3M | 40° C./75%/6M |
|---|---|---|
| Maximum Individual Impurity | 0.13 | 0.15 |
| Total Impurity | 0.29 | 0.50 |

This shows that not only antioxidants but other treatments to the product are also playing an important role to stabilize the product.

In the present invention at least antioxidant used includes also other than monothioglycerol. L-cysteine and thioglycolic acid, selected from the group comprising of acetyl cysteine, butylated hydroxy toluene, butylated hydroxy anisole. DL-tocopherol, sodium metabisulfite, sodium formaldehyde sulfoxylate, EDTA and its derivatives, methionine, ascorbic acid, citric acid and its pharmaceutically acceptable salt, sodium sulfite and its derivative and the like.

The formulation of present invention exhibits acceptable stability, retains a pharmaceutically desirable appearance, maintains the desired enantiomeric stability. Further, the formulation provided herein, is suitable for parental dosage.

The present invention particularly provides a pharmaceutical composition comprising:
a) pemetrexed in the range of 5-100 mg/ml
b) at least one antioxidant up to 10 mg/m wherein antioxidant also other than monothioglycerol, L-cysteine and thioglycolic acid, selected from the group comprising of acetyl cysteine, butylated hydroxy toluene, butylated hydroxy anisole, DL-tocopherol, sodium metabisulfite, sodium formaldehyde sulfoxylate, EDTA and its derivatives, methionine, ascorbic acid, citric acid and its pharmaceutically acceptable salt, sodium sulfite and its derivative etc.; and
c) a pharmaceutically acceptable excipient Liquid composition of pemetrexed mentioned above is optionally prepared by using the process of terminal sterilization.

"Pemetrexed" refers to the stable salts, acids and free base forms thereof including free acid, the pharmaceutically acceptable alkali metal, alkaline earth metal, non-toxic metal, ammonium, and substituted ammonium salts etc. In the present invention preferred salt of pemetrexed is disodium or dipotassium salt.

"Pharmaceutically acceptable excipient" includes a pharmaceutically acceptable carrier, diluents, solution or additive known to the skilled art and suitable for parenteral administration like saline, sodium chloride, mannitol and the like.

Pharmaceutically acceptable excipients may include osmolarity adjusting agent, stabilizing agent, optionally chelating agent, pH adjusting agent, optionally buffering agent, vehicle, etc.

In present invention osmolarity adjusting agent used may include but not limited to mannitol, sodium chloride, sucrose, dextrose, or combination thereof etc.

Stabilizing agent used may include but not limited to mannitol, sodium chloride, disodium edetate, D,L-Methionine, diethanolamine, human serum albumin tromethamine and the like.

Chelating agent if used may include but not limited to calcium disodium ethylene diamine tetra acetic acid, disodium ethylene diamine tetra acetic acid, sodium ethylene diamine tetra acetic, acid, diethylenetriaminepenta acetic acid and calteridol and the like.

Buffering agent if used may include but not limited to Phosphate buffer, acetate buffer, glycine buffer and tromethamine buffer and the like.

Osmolarity agent may include but not limited to Sodium chloride, dextrose, mannitol, sodium citrate and the like.

Further, pH adjusting agent may include sodium hydroxide, hydrochloric acid, sodium carbonate, citric acid, tromethamine, potassium hydroxide, sodium citrate etc.

Water for injection, any suitable solvent, etc. was used as a vehicle.

It is generally preferred that the process for preparing the formulation includes the use of a purge of an inert gas. Such inert gases are for example, nitrogen, argon, and the like.

The present invention further relates to a novelty that product prepared by our invention can withstand terminal sterilization where head space oxygen level less than 5% and dissolved oxygen less than 2 ppm with each individual impurity level in the final product less than 0.5%.

Below table represents the composition of present invention.

| Sr. No. | Ingredient | % |
|---|---|---|
| 1 | API | 1-10 |
| 2 | Stabilizing agent | 0-10 |
| 3 | Anti-oxidant | 0.1-2 |
| 4 | Osmolarity adjusting agent | 0-10 |
| 5 | pH adjusting agent | Q.S. |
| 6 | Water for injection | Q.S. |
| 7 | Inert gas | Q.S. |

Process for preparation of liquid dosage form of pemetrexed used in the present invention includes following steps but not limited to:
1. Prepare bulk solution by adding all excipients and API in pharmaceutically acceptable water, attain dissolve oxygen level below 2 ppm
2. Attain pH between 6-8
3. Filter and fill in the vial, attain head space oxygen less than 5%
4. Sterilize the solution by steam sterilization with $F_0$ value 1-30 min.

EXAMPLES

The present invention can be described by way of example only. It is to be recognized that modifications falling within the scope and spirit of the description or claims, which would be obvious to a person skilled in the art based upon the disclosure herein, are also considered to be included within the scope of this disclosure.

| Ingredient | Example 1 | Example 2 | Example 3 | Example 4 | Example 5 |
|---|---|---|---|---|---|
| Pemetrexed | 10 mg/ml | 10 mg/ml | 10 mg/ml | 10 mg/ml | 10 mg/ml |
| Mannitol | 10 mg/ml | 10 mg/ml | 10 mg/ml | 10 mg/ml | 10 mg/ml |
| Methionine | — | — | 2 mg/ml | — | — |
| Monothioglycerol | 1 mg/ml | 1 mg/ml | — | — | — |
| NaCl | 9 mg/ml | 9 mg/ml | 9 mg/ml | — | 9 mg/ml |
| Sodium DiSulfite | — | — | — | 1.0 mg/ml | — |
| Disodium EDTA | — | — | — | — | 0.1-0.25 mg/ml |
| Ascorbic acid | — | 2 mg/ml | 2 mg/ml | — | — |
| Inert gas | Q.S. | Q.S. | Q.S. | Q.S. | Q.S. |
| Water for injection | Q.S. | Q.S. | Q.S. | Q.S. | Q.S. |

For the above mentioned examples pH is between 6 and 8.

In all above mentioned examples an individual impurity lever attained is not more than 0.5%.

|  | Example 1 | Example 2 | Example 3 | Example 4 | Example 5 |
|---|---|---|---|---|---|
| Maximum Individual Impurity | 0.54 | 0.18 | 0.30 | 0.32 | 0.04 |
| Total Impurity | 2.7 | 0.74 | 1.2 | 1.7 | 0.17 |

One more trial of liquid composition of pemetrexed we have taken using L-cysteine HCl and other pharmaceutically acceptable excipients using the same process of preparation mentioned above wherein pH is maintained 7.4. The formulation is stable at room temperature. Maximum individual impurity level in this formulation is 0.15% and total impurity level in this formulation is 0.50% at 6M 40° C./75% RH.

We claim:

1. A liquid composition comprising:
    (a) 5 mg/mL to 100 mg/mL of pemetrexed, or its pharmaceutically acceptable salts;
    (b) L-cysteine, or salt thereof;
    (c) a pharmaceutically acceptable excipient;
    (d) less than 5% v/v of head space oxygen;
    (e) less than 2 parts per million (ppm) of dissolved oxygen; and
    (f) less than 1% w/w total impurities,
    wherein said liquid composition does not contain a chelating agent; and
    wherein the total impurities remain at less than 1% w/w for at least one month when stored at room temperature.

2. The liquid composition of claim 1, wherein the pharmaceutically acceptable excipient is selected from the group consisting of an osmolarity adjusting agent, a stabilizing agent, a pH adjusting agent, a vehicle, and combinations thereof.

3. The liquid composition of claim 1, wherein the chelating agent is selected from the group consisting of ethylene diamine tetraacetic acid or a salt thereof, diethylene triamine pentaacetic acid or a salt thereof, calteridol or a salt thereof, and combinations thereof.

4. The liquid composition of claim 3, wherein the composition is prepared using a process of terminal sterilization.

5. The liquid composition of claim 4, wherein said terminal sterilization is steam sterilization with an $F_0$ value of from 1 minute to 30 minutes.

6. The liquid composition of claim 1, wherein the composition comprises less than 0.5% w/w total impurities.

7. A liquid composition comprising:
    (a) about 10 mg/mL of pemetrexed;
    (b) about 1 mg/mL of L-cysteine hydrochloride;
    (c) a pharmaceutically acceptable excipient;
    (d) less than 5% v/v of head space oxygen;
    (e) less than 2 parts per million (ppm) of dissolved oxygen; and
    (f) less than 1% w/w total impurities,
    wherein said liquid composition does not contain a chelating agent; and
    wherein the total impurities remain at less than 1% w/w for at least one month when stored at room temperature.

8. The liquid composition of claim 7, wherein the pharmaceutically acceptable excipient is selected from the group consisting of an osmolarity adjusting agent, a stabilizing agent, a pH adjusting agent, a vehicle, and combinations thereof.

9. The liquid composition of claim 7, wherein said chelating agent is selected from the group consisting of ethylene diamine tetraacetic acid or a salt thereof, diethylene triamine pentaacetic acid or a salt thereof, calteridol or a salt thereof, and combinations thereof.

10. The liquid composition of claim 7, wherein the composition comprises less than 0.5% w/w total impurities.

11. A process for preparing the liquid composition of claim 1, comprising:
    (a) preparing a solution mixture comprising:
        (i) 5 mg/mL to 100 mg/mL of pemetrexed or its pharmaceutically acceptable salts,
        (ii) L-cysteine or salt thereof;
        (iii) a pharmaceutically acceptable excipient; and
        (iv) less than 1% w/w total impurities,
        under conditions to maintain dissolved oxygen level of 2 parts per million (ppm) or less; and
    (b) filtering and filling a vial with the solution of step (a) and maintaining head space oxygen of less than 5% v/v to produce the liquid composition.

12. The process of claim 11, further comprising the step of sterilizing the filtered solution by steam sterilization with an $F_0$ value of from 1 minute to 30 minutes.

13. The process of claim 11, wherein the solution mixture comprises less than 0.5% w/w total impurities.

14. The liquid composition of claim 1, wherein the pH of the composition is between 6 and 8.

15. The liquid composition of claim 14, wherein the pH of the composition is about 7.4.

16. The liquid composition of claim 7, wherein the pH of the composition is between 6 and 8.

17. A liquid composition comprising:
    (a) 5 mg/mL to 100 mg/mL of pemetrexed, or its pharmaceutically acceptable salts;
    (b) L-cysteine, or salt thereof;
    (c) a pharmaceutically acceptable excipient;
    (d) less than 5% v/v of head space oxygen;
    (e) less than 2 parts per million (ppm) of dissolved oxygen; and
    less than 1% w/w total impurities,
    wherein said liquid composition does not contain a chelating agent; and
    wherein said liquid composition is stable for at least one month when stored at room temperature.

18. A liquid composition comprising:
    (a) about 10 mg/mL of pemetrexed;
    (b) about 1 mg/mL of L-cysteine hydrochloride;
    (c) a pharmaceutically acceptable excipient;
    (d) less than 5% v/v of head space oxygen;
    (e) less than 2 parts per million (ppm) of dissolved oxygen; and
    (f) less than 1% w/w total impurities,
    wherein said liquid composition does not contain a chelating agent; and
    wherein said liquid composition is stable for at least one month when stored at room temperature.

* * * * *